(12) United States Patent
Cadossi et al.

(10) Patent No.: US 6,436,042 B1
(45) Date of Patent: *Aug. 20, 2002

(54) ULTRASONIC MEASURING DEVICE FOR DETERMINING BONE DENSITY AND STRUCTURE

(75) Inventors: Ruggero Cadossi, Carpi; Stefano Battista, Genoa; Alessandro Corsi, S. Martino; Antonio Dorati, Modena, all of (IT); Claus-C. Glüer, Hamburg; Reinhard Barkmann, Flintbek, both of (DE)

(73) Assignee: IGEA S.r.l., Carpi (IT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/066,145

(22) Filed: Apr. 24, 1998

(30) Foreign Application Priority Data

Apr. 24, 1997 (IT) .......................................... T097A0362

(51) Int. Cl.⁷ ................................................. A61B 8/00
(52) U.S. Cl. ........................ 600/438; 600/449; 600/459
(58) Field of Search ................................. 600/437, 438, 600/442, 449, 459; 73/597, 599

(56) References Cited

U.S. PATENT DOCUMENTS

| | | | | |
|---|---|---|---|---|
| 4,976,267 A | * | 12/1990 | Jeffcott et al. | 600/438 |
| 5,054,490 A | * | 10/1991 | Rossman et al. | 600/449 |
| 5,197,475 A | * | 3/1993 | Antich et al. | 600/444 X |
| 5,396,891 A | * | 3/1995 | Whitney et al. | 600/449 |
| 5,564,423 A | * | 10/1996 | Mele et al. | 600/449 X |
| 5,730,135 A | * | 3/1998 | Otani et al. | 600/449 |

FOREIGN PATENT DOCUMENTS

| | | |
|---|---|---|
| EP | 0 576 217 A1 | 12/1993 |
| EP | 0 663 182 | 7/1995 |
| GB | 2 257 253 A | 1/1993 |

* cited by examiner

Primary Examiner—Francis J. Jaworski
(74) Attorney, Agent, or Firm—Kinney & Lange, P.A.

(57) ABSTRACT

An ultrasonic measuring device and method for determining bone density and structure includes an electronic control unit, a positioning unit housing at least a transducer pair and carrying a receiving unit, the unit being adapted to be coupled to a bone segment of the human body and carrying a locating device for ascertaining the position of the bone segment with respect to the unit, and an electronic unit for determining a first waveform representing an ultrasonic signal transmitted through the metaphysis portion of the bony segment and a second waveform representing an ultrasonic signal transmitted through the diaphysis portion, and an electronic processor and display for displaying the first and second waveforms as a measured output.

21 Claims, 6 Drawing Sheets

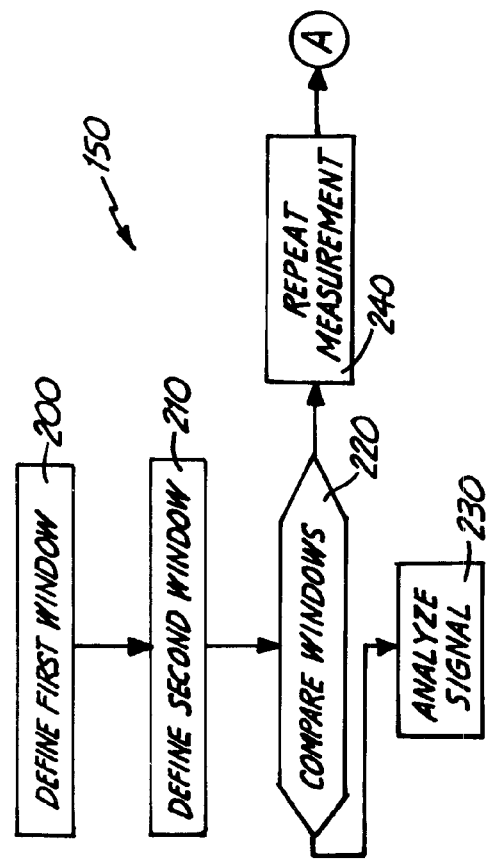
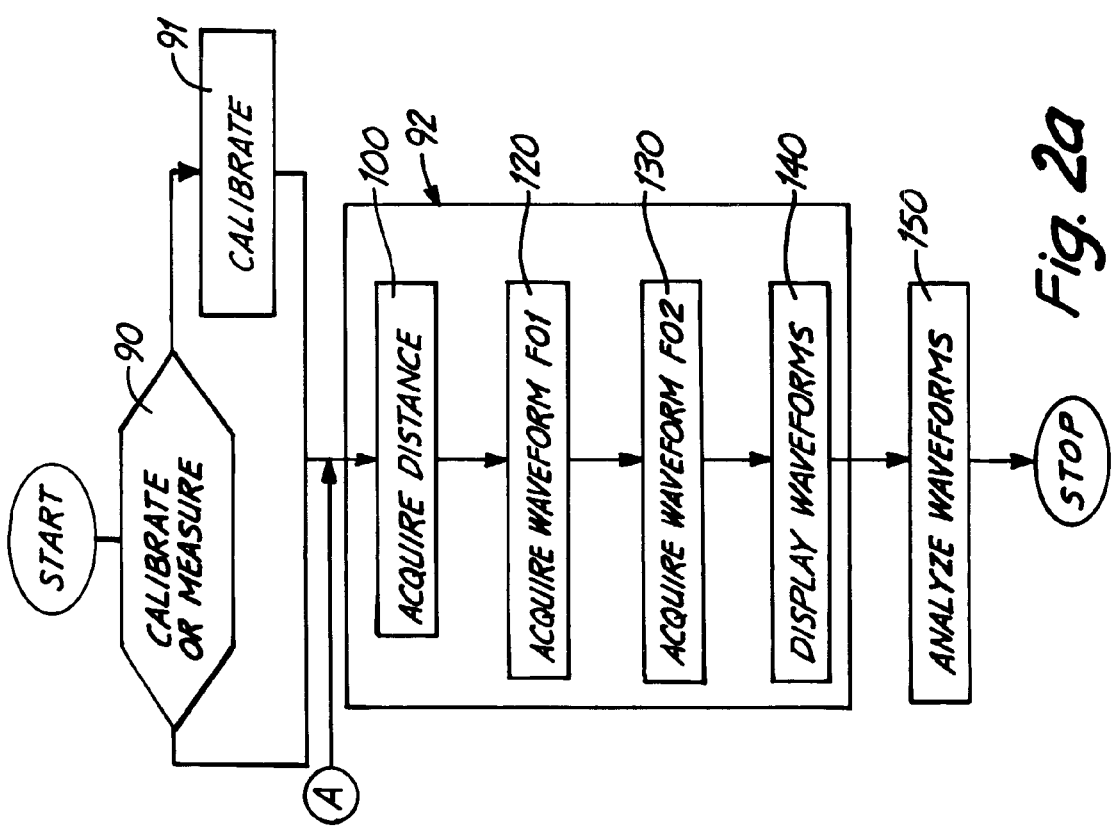
Fig. 2b
Fig. 2a

ULTRASONIC MEASURING DEVICE FOR DETERMINING BONE DENSITY AND STRUCTURE

BACKGROUND OF THE INVENTION

The present invention relates to an ultrasonic measuring device for determining bone density and structure.

Electronic devices for examining bone tissue and structure are known, which comprise an ultrasonic transducer for feeding pulses into a bone segment for examination (e.g. a finger); a receiver for picking up the pulses that have traveled through the bone segment; and processing circuits for representing the waveform and, given the distance between the transducer and the receiver, calculating the speed of the ultrasonic signal through the bone segment. As the transmission speed of the ultrasonic signal is greatly affected by the characteristics of the bone segment between the transducer and the receiver, and varies alongside a variation in bone structure and density, known devices compare the measured speed value with a reference value to determine a variation in bone structure and density, which normally indicates demineralization of the bone tissue (caused, for example, by osteoporosis). The waveform is also examined by a skilled technician to obtain information, albeit approximate and at times ambiguous, concerning the characteristics of the bone segment. As such, known devices fail to provide for precise analysis closely related to the characteristics of the bone tissue, and interpretation is further complicated in the event the bone segment comprises a distal portion. That is, the distal portion of a bone (FIG. 8) is known to comprise a substantially solid first end portion A (metaphysis) defined by a shell of thin cortical bone containing mainly bone trabeculae; and a more proximal, substantially tubular second portion B (diaphysis) comprising an outer tubular (cortical) portion defining an inner canal containing few bone trabeculae, which, in adults, are reabsorbed to hollow out the canal of the second portion.

A known device measuring the above distal portion produces a waveform and calculates the ultrasonic speed of an ultrasonic signal traveling indifferently through the first and second portions, which, as stated, have entirely different structures. As certain bone diseases, however, have a widely differing effect on the first and second portions, a separate analysis of the structural characteristics of the first (metaphysis) and second (diaphysis) portions would be extremely beneficial.

SUMMARY OF THE INVENTION

It is an object of the present invention to provide an ultrasonic measuring device for determining bone density and structure, designed to overcome the drawbacks of known devices by, among other things, discriminating between the characteristics of the first and second portion.

According to the present invention, there is provided an ultrasonic measuring device for determining bone density and structure, as claimed in claim 1.

The present invention also relates to a method of determining bone density and structure, as claimed in claim 12.

BRIEF DESCRIPTION OF THE DRAWINGS

A preferred non-limiting embodiment of the present invention will be described by way of example with reference to the accompanying drawings, in which:

FIGS. 2a, 2b, 2c show logic operating block diagrams of the FIG. 1 device;

DETAILED DESCRIPTION OF THE INVENTION

Figure 1:
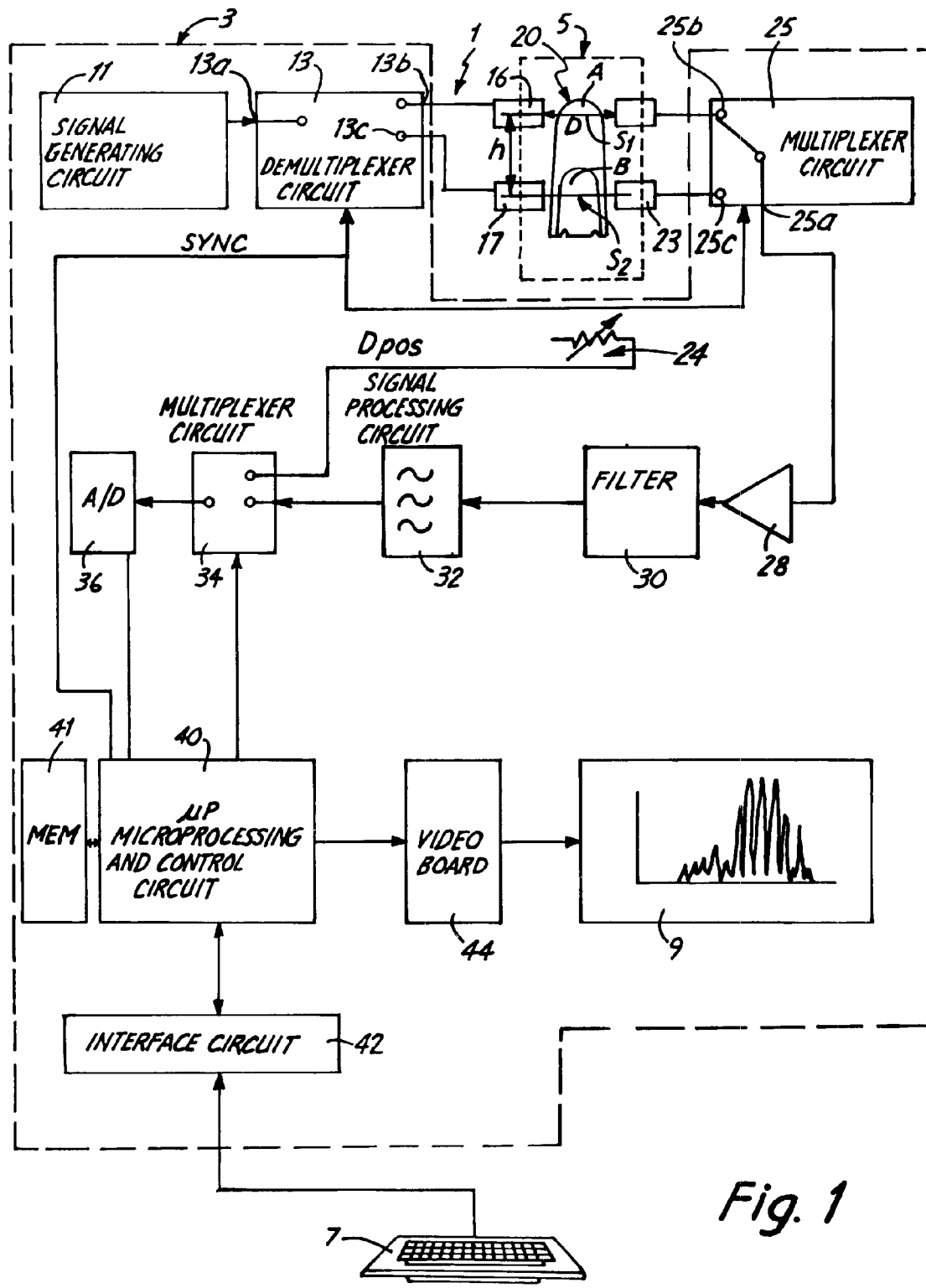
FIG. 1 shows, schematically, an ultrasonic measuring device for determining bone density and structure in accordance with the teachings of the present invention.

Number 1 in FIG. 1 indicates as a whole an electronic ultrasonic measuring device for determining bone density and structure, and comprising a central unit 3 housed in a parallelepiped casing (not shown), connected to a positioning gage 5 (shown schematically in FIG. 1), and having a keyboard 7 and a video terminal 9.

The central unit comprises a signal generating circuit 11 for generating a periodic signal of given frequency and highly constant amplitude, and which, in the example embodiment shown, generates a periodic pulse signal of 0.8 to 15 MHz frequency, e.g. 1.25 MHz. The output of circuit 11 communicates with the input 13a of a demultiplexer circuit 13, which has two outputs 13b, 13c communicating respectively with a first and a second piezoelectric transducer 16, 17 carried by positioning gage 5 and each for generating, in response to the periodic pulse signal at the input, an ultrasonic signal which is fed to a portion 20 of the human body (shown schematically) placed inside gage 5 (as described later on). Transducers 16 and 17 are separated by a constant distance h, so that the ultrasonic signals generated by them travel along straight parallel propagation paths S1, S2 also separated by distance h, and may generate synchronized ultrasonic signals or ultrasonic pulses at different instants.

First transducer 16 is connected to a first ultrasonic receiver 22 carried by gage 5 and facing first transducer 16 along path S1; second transducer 17 is connected to a second ultrasonic receiver 23 carried by gage 5 and facing second transducer 17 along path S2; and the facing respectively emitting and receiving surfaces of transducer 16 and receiver 22 and transducer 17 and receiver 23 are separated by a manually adjustable distance D. More specifically, distance D is measured by a position transducer 24 carried by positioning gage 5 and for generating a signal Dpos proportional to the measured value of distance D.

First and second ultrasonic receivers 22, 23 communicate respectively at the output with a first and a second input 25b, 25c of a multiplexer circuit 25, the output 25a of which communicates with the input of a signal amplifier 28; and demultiplexer and multiplexer circuits 13 and 25 are controlled synchronously by a remote signal SYNC, so as to connect input 13a to output 13b and input 25b to output 25a, or to connect input 13a to output 13c and input 25c to output 25a. The output of signal amplifier 28 is connected to the input of a filter 30 (in particular, a low-pass filter), the output of which is connected to a signal processing circuit 32 (e.g. another filter); and the output of circuit 32 is connected to a first input of a multiplexer circuit 34, the output of which is connected to an analog-digital converting circuit 36. Multiplexer circuit 34 also has other inputs, one of which is supplied with position signal Dpos from gage 5; and the output of converting circuit 36 communicates with an input of a microprocessor processing and control circuit 40, which, among other things, controls demultiplexer circuit 13, multiplexer circuit 25 and multiplexer circuit 34, communicates with keyboard 7 via an interface circuit 42, and supplies control signals to a video board 44 driving video terminal 9.

Figure 3:
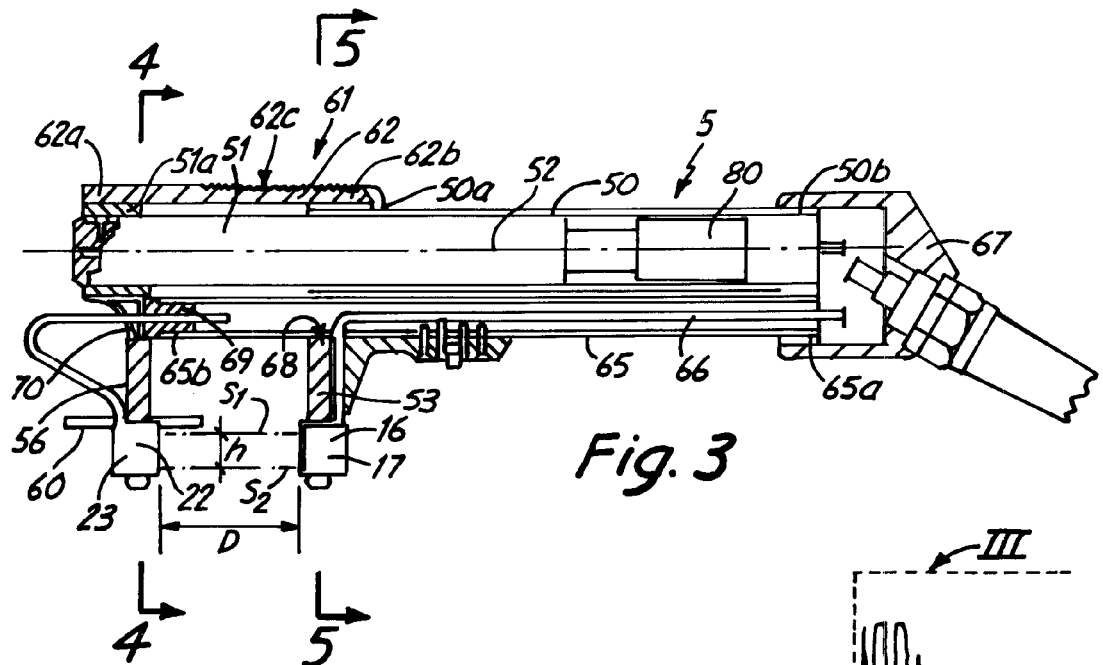
FIG. 3 shows a longitudinal section of an ultrasonic gage of the measuring device according to the present invention.

With reference to FIG. 3, number 5 indicates as a whole ultrasonic gage 5, which comprises a first outer tubular body 50 connected telescopically to a second inner tubular body 51 coaxial with, and sliding with respect to, body 5 along an axis 52.

First tubular body 50 has a first threaded free end 50a from which extends a first radial appendix 53 comprising a substantially parallelepiped base portion 53a with a threaded through hole 54 engaged by end 50a, and a straight portion 53b extending radially from base portion 53a. The free end of straight portion 53b has a through hole 55 engaged by a parallelepiped container housing first and second piezoelectric transducers 16, 17.

Second tubular body 51 projects from body 50 and terminates with an end portion 51a supporting a second radial appendix 56 facing first appendix 53, and which comprises a substantially parallelepiped base portion 56a integral with end 51a, and a straight portion 56b extending radially from base portion 56a. The free end of straight portion 56b has a through hole 57 engaged by a cylindrical tubular container housing first and second ultrasonic receivers 22, 23.

Second appendix 56 has a pair of through holes 58 extending close to an end edge of hole 57. More specifically, through holes 58 are located along an axis d1 perpendicular to the central longitudinal axis d2 of the appendix, and are symmetrical with axis d2.

Each hole 58 houses an end portion of a cylindrical rod 60 extending between second and first appendixes 56, 53 and parallel to axis 52. Rods 60 therefore extend parallel to each other, are separated by a distance substantially equal to the distance, measured along axis d1, between holes 58, and define a locating element for correctly positioning (as described later on) a portion of the human body, in particular a finger, with respect to appendixes 53, 56, transducers 16, 17, and receivers 22, 23. The portion of the human body used for measurement purposes may comprise the distal femur, in the case of measurements performed on newborn or premature babies, and the epiphysis of the index finger in the case of measurements for determining diseases relating to rheumatoid arthritis. Whichever the case, the examination region comprises a metaphysis and a diaphysis portion.

Holes 58 are so located that, when a finger is placed in the gage with a portion contacting both rods 60, an end bone portion of the finger is centered between transducers 16, 17 and receivers 22, 23.

Gage 5 also comprises a device 61 for manually adjusting the distance D between transducers 16, 17 and receivers 22, 23.

Device 61 comprises a rectangular blade 62 having a first free end 62a fixed stably to base portion 56a by means of screws, and a second free end 62b housed inside a rectangular groove 64 formed in base portion 53a. Blade 62 is slightly arc-shaped and presses on the bottom portion (not shown) of groove 64.

Blade 62 also comprises a toothed mid portion 62c; and gage 5 comprises a tube 65 carried by body 50 and extending along an axis 66 parallel to axis 52. More specifically, tube 65 comprises a first end portion 65a carried by an end body 67 integral with a second end 50b of tubular body 50; an intermediate portion engaging a through hole 68 formed in appendix 53 and coaxial with axis 66; and a second end portion 65b adjacent to portion 51a of body 51, and which terminates with an opening closed by a plug 69 with a hole, and also engages a through hole 70 formed in appendix 56 and coaxial with axis 66.

Tube 65 houses the cables supplying the energizing signal to transducers 16, 17, and the cables supplying the output signal to receivers 22, 23.

Transducer 24 is defined by a linear potentiometer (not shown) housed inside, and for determining the relative position of, tubular bodies 50, 51 to measure distance D and generate position signal Dpos.

An elastic element 80 (shown schematically) is interposed between bodies 50 and 51 to retain body 51 inside body 50 and push appendixes 53, 56 into contact with each other. The elastic force exerted by elastic element 80 may be adjustable.

The general operation of device 1 will now be described with reference to the FIG. 2a block diagram, which shows a series of operating steps controlled by microprocessor circuit 40.

To begin with, a block 90 enquires—the enquiry being displayed on video terminal 9—whether device 1 is to be calibrated or a measuring session performed.

If calibration is selected, block 90 goes on to a block 91, which starts the device calibration procedures in known manner. Conversely, block 90 goes on to a block 92, which performs a series of bone density and structure measuring operations. Once the device is calibrated, block 91 also goes on to block 92.

To perform the measurements in block 92, appendixes 53 and 56 are parted manually using device 61 in opposition to elastic element 80.

A first phalanx of one finger is then placed between transducers 16, 17 and receivers 22, 23, with the back of the phalanx contacting both rods 60. In this position, the axis of the finger is roughly perpendicular to axis 52 of the gage and to propagation paths S1 and S2, and the distal metaphysis of the phalanx is located between transducers 16, 17 and receivers 22, 23.

The distal portion of the phalanx is known to comprise a substantially solid first end portion A (metaphysis) defined by a shell of thin cortical bone containing mainly bone trabeculae; and a more proximal, substantially tubular second portion B (diaphysis) comprising an outer tubular (cortical) portion defining an inner canal containing few bone trabeculae. In adults, the canal of portion B is known to be hollowed out by reabsorption of the bone trabeculae, and portion A is also hollowed out later, though never completely.

In the position described above, propagation path S1 therefore extends through first portion A, and propagation path S2 through second portion B adjacent to portion A, i.e. the ultrasonic signal produced by transducer 16 travels mainly through the bone portion rich in trabeculae, while the ultrasonic signal produced by transducer 17 travels mainly through the inner canal surrounded by the cortical portion.

When device 61 is released, appendixes 53 and 56 are pushed by the elastic element on to opposite lateral portions of the finger, with transducers 16, 17 and receivers 22, 23 on either side of the finger. In this position, the distal portion (and hence the bone tissue) of the finger is positioned stably with respect to gage 5 and prevented from moving laterally by appendixes 53, 56 pressing on either side of the finger; gage 5 is prevented by rods 60 from sliding downwards towards the palm side of the hand, and is prevented by the condyles from sliding outwards; and transducers 16, 17 and receivers 22, 23 are positioned in parallel facing planes.

Positioning the finger as described above provides, for each measurement, for correctly positioning portions A and B of the bone tissue with respect to transducers 16, 17.

With reference to FIG. 2a, block 92 comprises a block 100, which provides for automatically acquiring distance D between transducers 16, 17 and receivers 22, 23. More specifically, the (analog) signal generated by potentiometer 24 is supplied, via multiplexer 34, to converter 36, which supplies microprocessor 40 with the digital value of distance D, which may be displayed on video 9 and used later for calculating other parameters.

Block 100 is followed by a first measuring block 120, which acquires and displays on video 9 the waveform of the ultrasonic signal received by receiver 22.

More specifically, block 120 of microprocessor circuit 40 sets demultiplexer 13 and multiplexer 25 to a first position in which input 13a is connected to output 13b, and input 25b to output 25a; the alternating signal supplied by circuit 11 to transducer 16 produces a stream of ultrasonic waves along path S1 through portion A (the trabecular portion) of the bone to receiver 22; and the signal generated by receiver 22 is voltage-amplified by amplifier 28, filtered by filter 30, possibly processed by circuit 32, digitized by converter 36, and supplied to microprocessor circuit 40.

Microprocessor circuit 40 effects (in known manner) a cartesian reconstruction (FIG. 6a) of the waveform FO1 of the ultrasonic signal received by receiver 22, wherein the X axis represents a time scale and the Y axis an amplitude scale, with time and amplitude values increasing outwards of the origin.

The cartesian representation of waveform FO1 of the signal through distal metaphysis portion A has been found by the inventors to comprise a first portion I (shown enclosed in a rectangle) in turn comprising a number of successive peaks Ptr (normally three or four); a second portion II (shown enclosed in a rectangle) adjacent to the first portion and in turn comprising a small number of peaks of substantially negligible amplitude; and a third portion III (shown enclosed in a rectangle) adjacent to second portion II and in turn comprising a large number of peaks generally of greater amplitude than those of first portion I.

The first portion I of waveform FO1 is assumed by the inventors to relate to the signal portion through the trabecular portion of the bone, and second portion II of the waveform to the signal portion through the cortical portion of the bone. As the received signal has traveled through portion A mainly comprising bone trabeculae, first portion I comprises a large amount of energy (significant peaks Ptr); second portion II comprises very little energy (almost negligible peaks); and third portion III mainly comprises noise caused by bouncing and reflection of the energizing signal. Waveform FO1 as illustrated is memorized (digitized) by block 120 in a buffer memory 41 communicating with microprocessor circuit 40.

First measuring block 120 is followed by a second measuring block 130, which acquires and displays on video 9 the waveform FO2 (FIG. 6b) of the ultrasonic signal received by receiver 23.

More specifically, microprocessor circuit 40 sets demultiplexer 13 and multiplexer 25 to a second position in which input 13a is connected to output 13c, and input 25c to output 25a; the alternating signal supplied by circuit 11 to transducer 17 produces a stream of ultrasonic waves along path S2 through portion B (the cortical portion and canal) of the bone to receiver 23; and the signal generated by receiver 23 is voltage-amplified by amplifier 28, filtered by filter 30, possibly processed by circuit 32, digitized by converter 36, and supplied to microprocessor circuit 40.

Microprocessor circuit 40 effects (in known manner) a cartesian reconstruction of the waveform of the ultrasonic signal received by receiver 23, as described above for the signal received by receiver 22.

The cartesian representation (FIG. 6b) of waveform FO2 of the signal through diaphysis portion B has been found by the inventors to comprise a first portion I' (shown enclosed in a rectangle) in turn comprising a small number of successive peaks of negligible amplitude; a second portion II' (shown enclosed in a rectangle) adjacent to the first portion and in turn comprising a number of peaks Pco; and a third portion III' (shown enclosed in a rectangle) adjacent to second portion II' and in turn comprising a large number of peaks generally of greater amplitude than those of the second portion.

The first portion I' of waveform FO2 is assumed by the inventors to relate to the signal portion through the trabecular portion of the bone, and second portion II' of the waveform to the signal portion through the cortical portion of the bone. As the received signal has traveled through portion B mainly comprising a cortical portion, second portion II' comprises a large amount of energy (significant peaks Pco); first portion I' comprises very little energy (almost negligible peaks); and third portion III' mainly comprises noise caused by bouncing and reflection of the energizing signal. Waveform FO2 as illustrated is memorized by block 130 in buffer memory 41.

Block 130 is followed by a block 140, which provides for displaying the acquired, memorized waveforms FO1 and FO2. More specifically, block 140 may:

display waveforms FO1 and FO2 alternately;

display both waveforms FO1 and FO2 separately in two different portions of video 9;

display both waveforms FO1 and FO2 superimposed in different colours in the same portion of video 9 and using the same reference system.

Block 140 therefore provides the user of device 1 with precise information concerning the examined bone portion, by displaying the waveforms of two widely differing adjacent portions (A and B). The presence of a characteristic, easily identifiable portion (I) in waveform FO1 provides information concerning the structure of the trabecular bone tissue portion; while the presence of a characteristic, easily identifiable portion (II') in waveform FO2 provides information concerning the characteristics of the cortical bone portion.

Before terminating the analysis, the present invention also provides for performing a series of automatic operations on waveforms FO1 and FO2 (block 150 following block 140).

Block 150 comprises a first block 200, which subjects waveform FO1 to a characteristic-pattern recognition process to define a window F1 (e.g. a rectangle) enclosing first portion I of waveform FO1, and to determine the time limits tI1 and tI2 of window F1 (defined as the points at which the window intersects the time axis). The pattern recognition process may be performed in known manner by determining, in first waveform FO1, the first group of adjacent peaks having, on either side, signal portions of a given substantially zero amplitude.

Block 200 is followed by a block 210, which subjects waveform FO2 to a characteristic-pattern recognition process to define a window F2 (e.g. a rectangle) enclosing second portion II' of waveform FO2, and to determine the time limits tII1 and tII2 of window F2 (defined as the points at which the window intersects the time axis). The pattern recognition process may be performed in known manner by determining, in second waveform FO2, the first group of adjacent peaks having, on one side, signal portions of a given substantially lower amplitude, and, on the other side, signal portions of a higher amplitude.

Block 210 is followed by a block 220, which compares windows F1 and F2 to automatically check the measurements are correct. More specifically, if first window F1 is substantially adjacent to second window F2 in a cartesian system having the same origin as the cartesian systems of waveforms FO1 and FO2, i.e. if tI2 is substantially equal to tII1, the measurement is considered correct, and block 220 goes on to a block 230. Conversely, block 220 goes on to a block 240, which displays a repeat-measurement message on the video, and then goes back to block 92 to perform another measuring cycle.

Block 230 performs a series of operations on the portions of waveforms FO1, FO2 in windows F1 and/or F2 to obtain information concerning bone density and structure, and whereby block 230 calculates (relative to windows F1 and F2):

the energy E of the signal within the window, by calculating the integral of the waveform portion in the window;

the number of peaks Np of the waveform portion in the window;

the width W of the window, measured along the X axis;

the peak-envelope slope SLP of the signal portion in the window;

the peak sharpness SH of the waveform portion in the window;

the maximum-peak value Vpm of the waveform portion in the window.

The values calculated in block 230 may be combined to obtain one or more indications of the bone tissue condition.

Figure 2C:
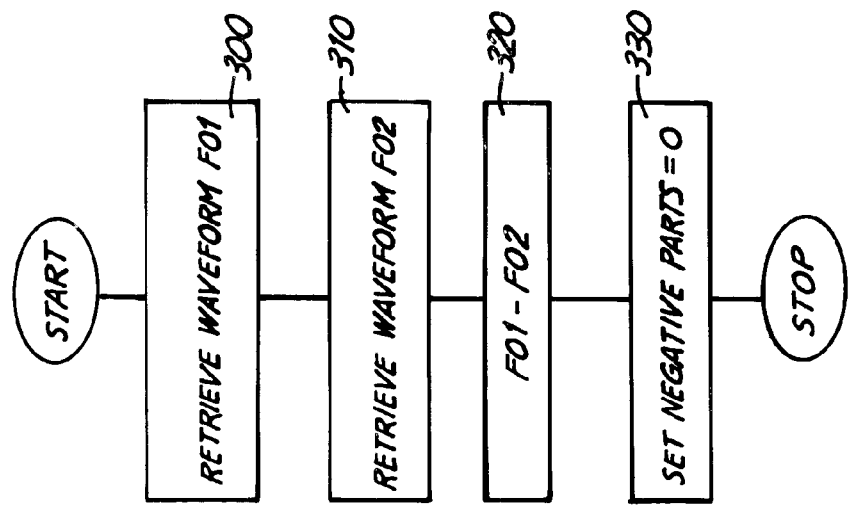

FIG. 2c shows a series of "clean-up" operations of waveforms FO1 and FO2, performed for example to improve the effectiveness of block 150, and which may conveniently be performed prior to the block 150 waveform analysis.

More specifically, the waveform "clean-up" operations comprise a first block 300, which retrieves digitized waveform FO1 from memory 41, and is followed by a block 310, which retrieves from memory 41 digitized waveform FO2.

Figure 6C:
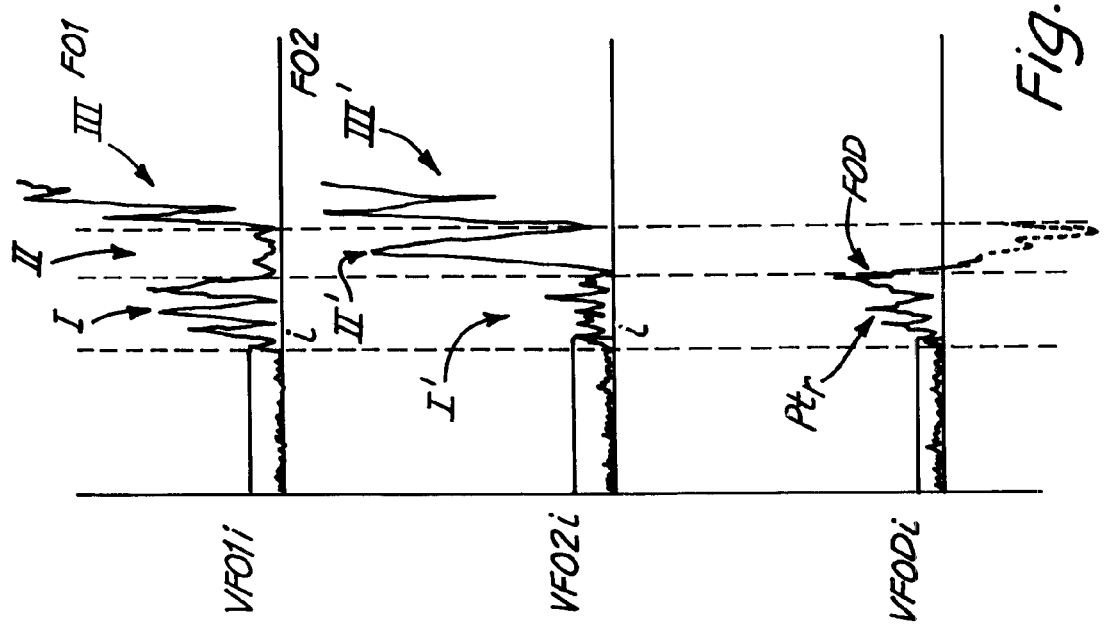
FIGS. 6a, 6b, 6c show signals acquired by the device according to the present invention.
Figure 6A:
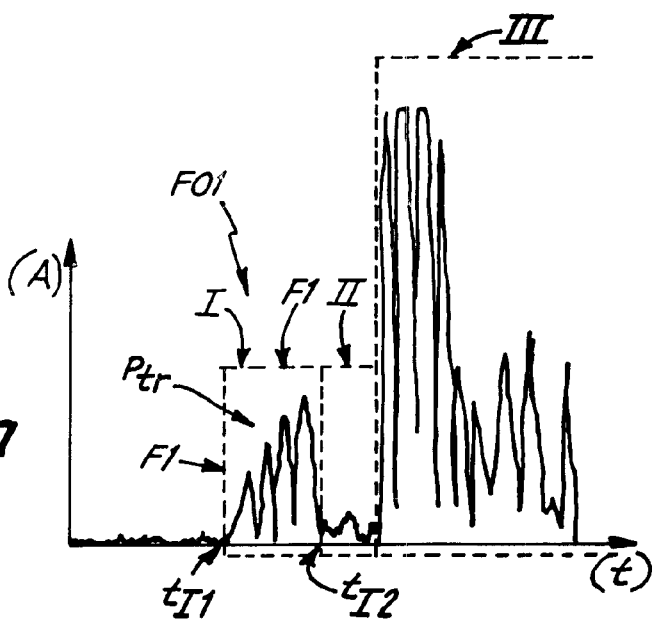
Figure 6B:
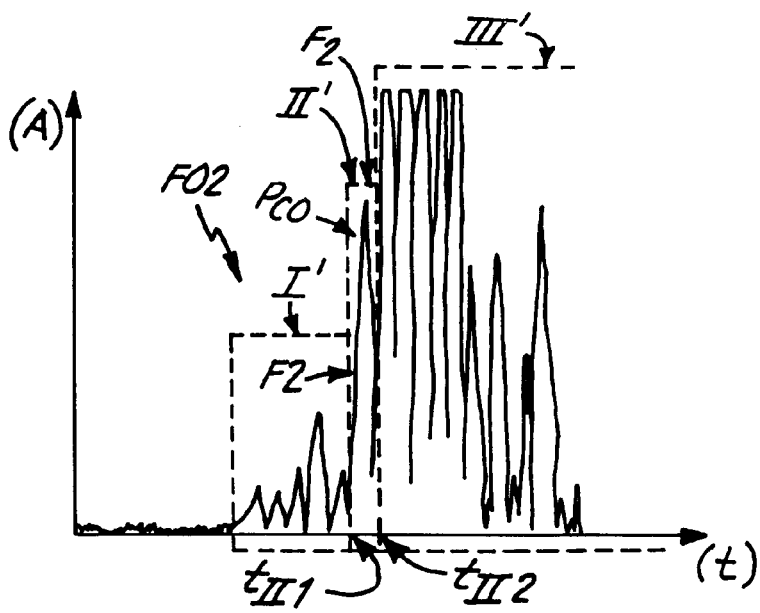
Figure 4:
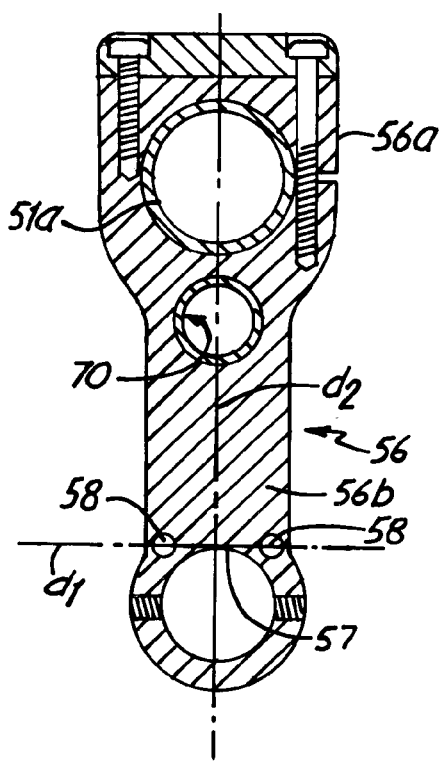
FIG. 4 shows a section of the gage along line IV—IV in FIG. 3.
Figure 5:
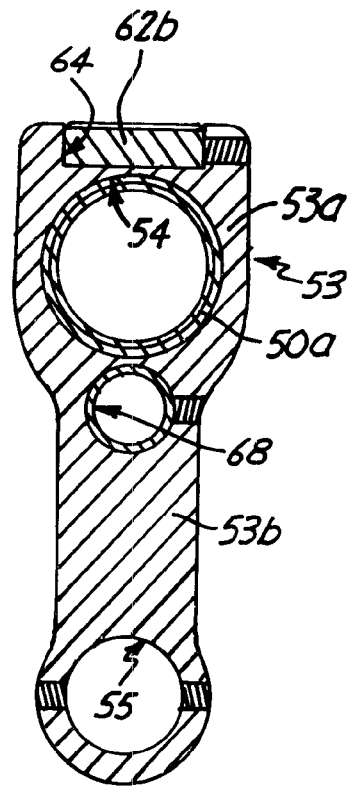
FIG. 5 shows a section of the gage along line V—V in FIG. 3.
Figure 8:
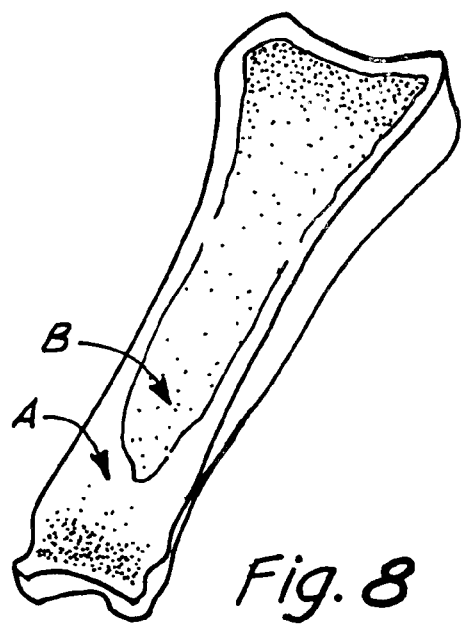
FIG. 8 shows a view in perspective of a portion of bone tissue.

Block 310 is followed by a block 320 in which, for each X-axis value "i" in the reference system of waveform FO1, the corresponding amplitude value VFO1i of waveform FO1 is determined; for a corresponding X-axis value "i" in the reference system of waveform FO2, the corresponding amplitude value VFO2i of waveform FO2 is determined; amplitude value VFO2i is subtracted from VFO1i, i.e. VFODi=VFO1i−VFO2i; the resulting value VFODi of the subtraction is assumed, for that particular X-axis point "i", to represent a new so-called difference waveform FOD; and the above operations are repeated for all the points "i" corresponding to Y-axis values of waveforms FO1 and FO2, so as to subtract waveform FO2 from waveform FO1 and generate difference waveform FOD (FIG. 6c).

Block 320 is followed by a block 330 in which each negative X-axis value of difference waveform FOD is made equal to zero to generate a corrected difference waveform for use in the waveform analysis in block 150.

The reason for the above operations lies in the peaks in portion II of waveform FO1, which, though of limited amplitude, may nevertheless interfere with the window-definition operations in block 200. The above operations, on the other hand, provide for subtracting from the peaks in portion II the peaks in corresponding portion II' to produce an obviously negative difference signal, which is converted by block 330 into a zero signal to form, in other words, a zero-amplitude portion to the right of the group of peaks Ptr in the difference signal, and so enable better selection of peaks Ptr. The above operations have substantially no effect on the amplitude of peaks Ptr in the difference signal, by portion I of waveform FO1 corresponding to a portion I' comprising peaks of very limited amplitude. Similarly, waveform FO1 may be subtracted from waveform FO2, and difference waveform FOD may be subjected to the same processing as in block 330.

The system according to the present invention therefore provides for eliminating the drawbacks typically associated with known systems.

The device described, in fact, provides for simultaneously measuring two adjacent bone portions (the distal metaphysis and adjacent proximal diaphysis portion) differing widely as to anatomical structure despite forming part of the same bone portion. Waveforms FO1 and FO2 also provide for discriminating between the two portions to obtain separate information relative to the distal metaphysis and the proximal diaphysis portion. Device 1 in fact provides for displaying and processing two different waveforms—FO1 and FO2—with clearly visible portions I and II', which may be analyzed and compared, even only visually, to obtain various information concerning the characteristics of the distal metaphysis and the proximal diaphysis portion.

The automatic operations performed in blocks 200, 210, 220 also provide for determining correct positioning of transducers 16, 17 and correct performance of the measurements, as well as for repeating any unconfirmed measurements. Automatically defining windows enclosing characteristic portions of the waveform enables signal-analysis algorithms (block 230) to be applied to characteristic waveform portions to obtain data accurately representing the condition of the bone tissue; and the operations in blocks 300–330 assist in accurately defining the windows.

Clearly, changes may be made to the device as described and illustrated herein without, however, departing from the scope of the present invention.

Figure 7:
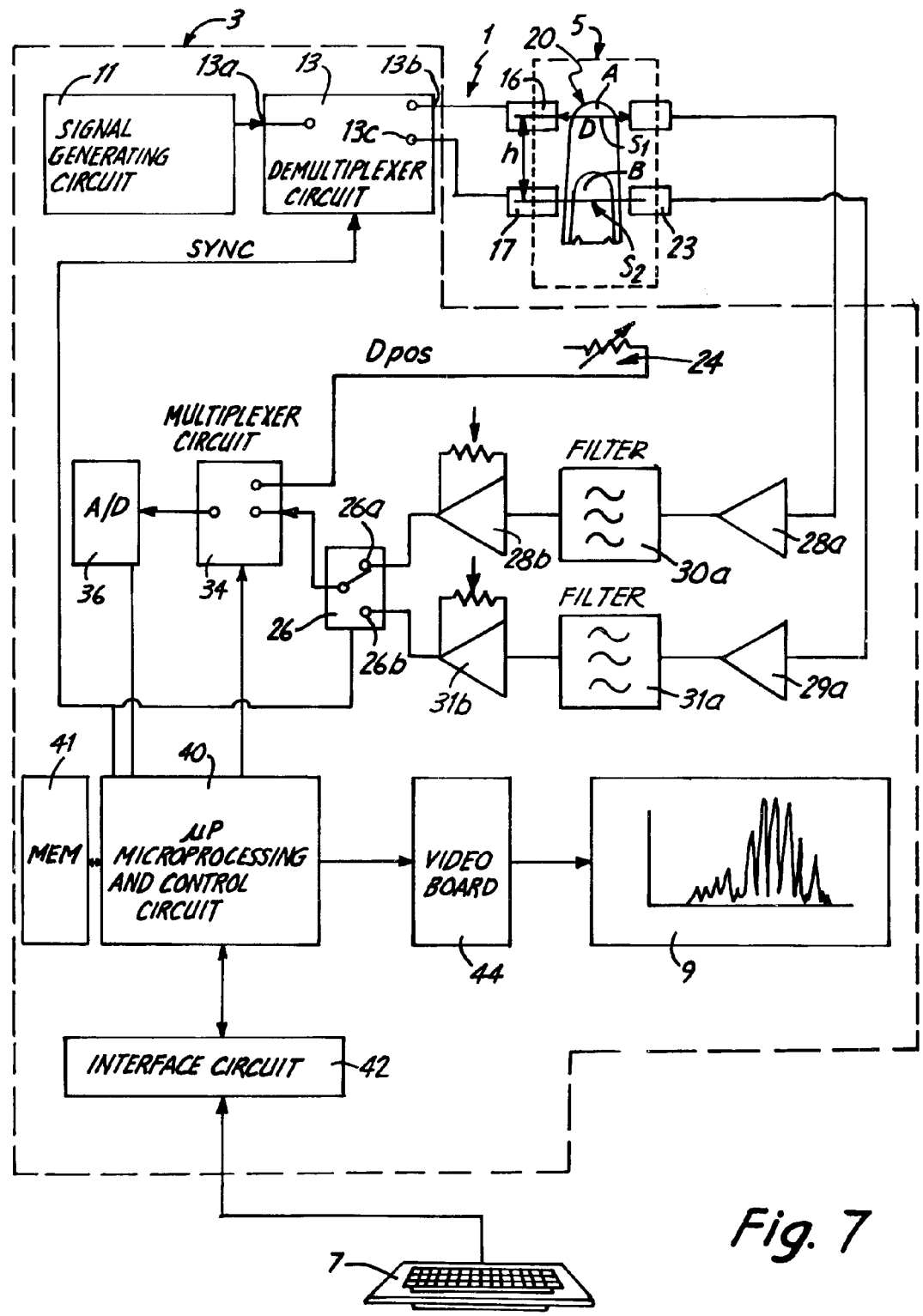
FIG. 7 shows, schematically, a variation of the FIG. 1 measuring device.

The device 1a shown in FIG. 7 differs from the FIG. 1 device by the output of first ultrasonic receiver 22 communicating directly with the input of a signal amplifier 28a, the output of which communicates with the input of a filter 30a (in particular a low-pass filter) having an output connected to the input of a variable-gain amplifier 28b; by the output of second ultrasonic receiver 23 communicating directly with the input of a signal amplifier 29a, the output of which communicates with the input of a filter 31a (in particular a low-pass filter) having an output connected to the input of a variable-gain amplifier 31b; and by the outputs of amplifiers 28b and 31b communicating respectively with a first and a second input 26a, 26b of a multiplexer circuit 26 having a single output connected to the input of multiplexer circuit 34. As for the rest, device 1a is identical to, and operates in the same way as, device 1 described with reference to FIG. 1, except that the signal generated by each ultrasonic receiver 22, 23 is amplified by a specific variable-gain amplifying chain (comprising amplifiers 28a,28b and 29a, 31b respectively) to enable the amplification factor of waveform FO1 to be varied independently from that of waveform FO2; and multiplexer circuit 26 provides for selecting one or other of the signals generated by receivers 22, 23.

We claim:

1. An ultrasonic measuring device for determining bone density and structure comprising:

an electronic control unit (3) having signal generating means (11) for generating an energizing signal;

a positioning unit (5) connected to said electronic control unit (3) and having at least a first and a second transducer (16, 17), each for generating an ultrasonic signal in response to said energizing signal; said first and said second transducer (16, 17) being separated by a constant distance (h), and generating respective ultrasonic signals which travel respectively along a first and a second propagation path (S1, S2) spaced (h) with respect to each other; and ultrasonic-signal receiving means (22, 23) carried by said positioning unit (5) and facing said first and said second transducer (16, 17) at an adjustable distance (D) from the first and second transducer (16, 17);

said positioning unit (5) adapted to be coupled to a bone segment of the human body, interposed between the first and second transducer (16, 17) and said ultrasonic-signal receiving means (22, 23); said bone segment comprising at least a substantially solid first metaphysis end portion (A) mainly defined by bone trabeculae, and a substantially tubular second diaphysis portion (B) adjacent to the first metaphysis portion (A) and in turn comprising a cortical portion defining an inner canal with substantially no bone trabeculae; said positioning unit (5) also comprising locating means (60) for positioning said bone segment with respect to said positioning unit so that said first propagation path (S1) extends through said first metaphysis portion (A) and said second propagation path (S2) extends through said second diaphysis portion (B);

said electronic unit (3) comprising signal processing means (28, 30, 32, 36, 40) connected to said ultrasonic-signal receiving means (22, 23) and for respectively determining a first waveform (FO1) representing the ultrasonic signal transmitted through said first metaphysis portion (A), and a second waveform (FO2) representing the ultrasonic signal transmitted through said second diaphysis portion (B); said signal processing means (28, 30, 32, 36, 40) also being connected to electronic processing and display means (40, 44, 9) for displaying said first (FO1) and said second (FO2) waveform as measured output.

2. A device as claimed in claim 1, characterized in that said electronic processing and display means (40, 44, 9) provide a cartesian representation of said waveforms, wherein the axes respectively define the time axis and amplitude of the received signal.

3. A device as claimed in claim 2, characterized by comprising processing means for processing the first and second waveforms (FO1, FO2) and comprising:

first retrieving means (300) for supplying a digitized first waveform (FO1);

second retrieving means (310) for supplying a digitized second waveform (FO2);

subtracting means (320) for subtracting from an amplitude value of the first waveform an amplitude value of the second waveform (VFO1i, VFO2i) having the same X-axis value; said subtracting means being selected cyclically for a number of successive X-axis values (i) to subtract the second waveform (FO2) from the first waveform (FO1) and generate a difference waveform (FOD); and normalizing means (330) for analyzing the difference waveform (FOD) and setting to a reference value each negative value of the difference waveform (FOD) to generate a corrected difference waveform for use in subsequent waveform analysis operations.

4. A device as claimed in claim 1, characterized in that said electronic processing and display means (40, 44, 9) display the first waveform (FO1) and the second waveform (FO2) alternately.

5. A device as claimed in claim 1, characterized in that said electronic processing and display means (40, 44, 9) display the first waveform (FO1) and the second waveform (FO2) in different portions of display means (9).

6. A device as claimed in claim 1, characterized in that said electronic processing and display means (40, 44, 9) display the first waveform (FO1) and the second waveform (FO2) in the same portion of display means (9) and with the same reference system, so as to superimpose said waveforms.

7. A device as claimed in claim 1, characterized in that said signal processing means (40) comprise first automatic recognition means (200) for determining in said first waveform (FO1) at least a first characteristic portion (I), and second automatic recognition means (210) for determining in said second waveform (FO2) at least a second characteristic portion (II'); said signal processing means (40) also comprising comparing means (220) for examining the relative location of said first and second characteristic portions (I, II') to determine correct performance of the signal acquisition operations.

8. A device as claimed in claim 7, characterized in that said first automatic recognition means (200) define a first window (F1) enclosing said first characteristic portion (I), and said second automatic recognition means (210) define a second window (F2) enclosing said second characteristic portion (II'); said comparing means (220) examining the relative location of said first and said second window.

9. A device as claimed in claim 1, wherein said first waveform (FO1), representing the signal through said first metaphysis portion (A), comprises a first portion (I) in turn comprising a number of successive peaks (Ptr); a second portion (II) adjacent to the first portion and in turn comprising a small number of peaks of substantially negligible amplitude; and a third portion (III) adjacent to the second portion (II) and in turn comprising a large number of peaks of generally greater amplitude than the peaks in the first portion; characterized by comprising automatic analyzing means (200) for automatically analyzing said first waveform and selecting in the first waveform at least said first portion (I).

10. A device as claimed in claim 1, wherein said second waveform (FO2), representing the signal through said second diaphysis portion (B), comprises a first portion (I') in turn comprising a small number of successive peaks of negligible amplitude; a second portion (II') adjacent to the first portion and in turn comprising a number of peaks (Pco); and a third portion (III') adjacent to the second portion (II') and in turn comprising a large number of peaks of generally greater amplitude than the peaks in the second portion; characterized by comprising automatic analyzing means (210) for automatically analyzing said second waveform and selecting in the second waveform at least said second portion (II').

11. A device as claimed in claim 1, characterized in that said positioning unit (5) comprises:

a first tubular body (50);

a second tubular body (51) coaxial with and slidable axially with respect to the first tubular body;

a first straight appendix (53) extending radially from an end portion (50a) of said first tubular body (50);

a second straight appendix (56) extending radially from an end portion (51a) of said second tubular body (51);

said appendixes (53, 56) facing each other and respectively carrying said first and second transducers (16, 17) and said signal receiving means (22, 23) facing each other at a distance (D) adjustable according to the relative position of said first (50) and second (51) tubular bodies.

12. An ultrasonic measuring method for determining bone density and structure comprising the steps of:

generating an energizing signal (11);

supplying said energizing signal to a first and a second transducer (16, 17), each for generating an ultrasonic signal in response to the input signal; said first and said second transducer (16, 17) being separated by a constant distance (h), and generating respective ultrasonic signals which travel respectively along a first and a second propagation path (S1, S2) spaced (h) with respect to each other;

coupling said first transducer (16) to a first portion (A) of a bone segment of the human body, said first portion (A) being substantially solid and mainly defined by bone trabeculae;

coupling said second transducer (17) to a second portion (B) of a bone segment of the human body, in particular a distal diaphysis of a phalanx of the hand; said second portion (B) comprising a cortical portion of the bone segment defining an inner canal with substantially no bone trabeculae;

detecting the ultrasonic signal that has traveled mainly through said first portion (A) along said first propagation path (S1) to generate a first input signal;

detecting the ultrasonic signal that has traveled mainly through said second portion (B) along said second propagation path (S2) to generate a second input signal; and processing said first and said second input signal to respectively display as measured output a first waveform (FO1) representing the ultrasonic signal transmitted through said first portion (A), and a second waveform (FO2) representing the ultrasonic signal transmitted through said portion (B).

13. A method as claimed in claim 12, characterized in that said step of processing said first and said second input signal comprises the step of displaying said waveforms in a cartesian reference system, the axes of which respectively define the time axis and amplitude of the received signal.

14. A method as claimed in claim 13, characterized by comprising a processing step to process the first and second waveforms (FO1, FO2) and comprising:

a retrieving step (300) to retrieve a digitized first waveform (FO1);

a retrieving step (310) to retrieve a digitized second waveform (FO2);

a subtracting step (320) to subtract from an amplitude value of the first waveform an amplitude value of the second waveform (VFO1i, VFO2i) having the same X-axis value; said subtracting step being repeated cyclically for a number of successive X-axis values (i) to subtract the second waveform (FO2) from the first waveform (FO1) and generate a difference waveform (FOD); and a normalizing step (330) to normalize the difference waveform (FOD) and set to a reference value in that said step of processing said first and said second input signal comprises the step of alternately displaying said first waveform (FO1) and said second waveform (FO2).

15. A method as claimed in claim 12, characterized in that said step of processing said first and said second input signal comprises the step of alternately displaying said first waveform (FO1) and said second waveform (FO2).

16. A method as claimed in claim 12, characterized in that said step of processing said first and said second input signal comprises the step of displaying the first waveform (FO1) and the second waveform (FO2) in different portions of display means (9).

17. A method as claimed in claim 12, characterized in that said step of processing said first and said second input signal comprises the step of displaying the first waveform (FO1) and the second waveform (FO2) in the same portion of display means (9) and with the same reference system, so as to superimpose said waveforms.

18. A method as claimed in claim 12, characterized in that said step of processing said first and said second input signal comprises the substeps of:

automatically recognizing at least a first characteristic portion (I) in said first waveform (FO1);

automatically recognizing at least a second characteristic portion (II') in said second waveform (FO2);

comparing the relative locations of said first and said second characteristic portion (I, II') to determine correct performance of the signal acquisition operations.

19. A method as claimed in claim 18, characterized in that said step of automatically recognizing at least a first characteristic portion (I) in said first waveform (FO1) comprises the step of defining a first window (F1) enclosing said first characteristic portion (I); said step of automatically recognizing at least a second characteristic portion (II') in said second waveform (FO2) comprising the step of defining a second window (F2) enclosing said second characteristic portion (II'); and said comparing step comprising the step of examining the relative location of said first and said second window.

20. A method as claimed in claim 12, wherein said first waveform (FO1), representing the signal through said first portion (A), comprises a first portion (I) in turn comprising a number of successive peaks (Ptr); a second portion (II) adjacent to the first portion and in turn comprising a small number of peaks of substantially negligible amplitude; and a third portion (III) adjacent to the second portion (II) and in turn comprising a large number of peaks of generally greater amplitude than the peaks in the first portion; characterized by comprising an automatic analyzing step (200) to automatically analyze said first waveform to select in the first waveform at least said first portion (I).

21. A device as claimed in claim 12, wherein said second waveform (FO2), representing the signal through said second portion (B), comprises a first portion (I') in turn comprising a small number of successive peaks of negligible amplitude; a second portion (II') adjacent to the first portion and in turn comprising a number of peaks (Pco); and a third portion (III') adjacent to the second portion (II') and in turn comprising a large number of peaks of generally greater amplitude than the peaks in the second portion; characterized by comprising an automatic analyzing step (210) to automatically analyze said second waveform to select in the second waveform at least said second portion (II').

* * * * *